(12) United States Patent
Asayama

(10) Patent No.: US 8,731,955 B2
(45) Date of Patent: May 20, 2014

(54) ULTRASONOGRAPHIC DEVICE

(75) Inventor: Keijiro Asayama, Kanagawa (JP)

(73) Assignee: Konica Minolta, Inc., Tokyo (JP)

( * ) Notice: Subject to any disclaimer, the term of this patent is extended or adjusted under 35 U.S.C. 154(b) by 1028 days.

(21) Appl. No.: 11/913,577

(22) PCT Filed: May 16, 2006

(86) PCT No.: PCT/JP2006/309752
§ 371 (c)(1),
(2), (4) Date: Nov. 5, 2007

(87) PCT Pub. No.: WO2006/123662
PCT Pub. Date: Nov. 23, 2006

(65) Prior Publication Data
US 2009/0094057 A1    Apr. 9, 2009

(30) Foreign Application Priority Data

May 19, 2005   (JP) ................................. 2005-146763

(51) Int. Cl.
*G06Q 50/00*    (2012.01)
(52) U.S. Cl.
USPC .................. 705/2; 705/3; 726/26; 726/27
(58) Field of Classification Search
USPC ................ 705/2–4; 713/193–194; 726/26–27
See application file for complete search history.

(56) References Cited

U.S. PATENT DOCUMENTS

| 6,306,089 | B1  |     | 10/2001 | Coleman et al. |         |
|-----------|-----|-----|---------|----------------|---------|
| 6,449,349 | B1  | *   | 9/2002  | Higuchi .................. | 379/100.17 |
| 6,574,629 | B1  | *   | 6/2003  | Cooke et al. .......................... | 1/1 |
| 6,678,764 | B2  | *   | 1/2004  | Parvulescu et al. ............. | 710/65 |
| 7,059,721 | B2  | *   | 6/2006  | Hayashi et al. ............... | 351/206 |
| 7,159,120 | B2  | *   | 1/2007  | Muratov et al. ............... | 713/182 |
| 7,418,602 | B2  | *   | 8/2008  | Yoshida et al. ............... | 713/193 |
| 2004/0138569 | A1 | * | 7/2004 | Grunwald et al. ............ | 600/459 |
| 2004/0153862 | A1 |   | 8/2004 | Grellmann et al. |  |
| 2004/0233930 | A1 | * | 11/2004 | Colby, Jr. ...................... | 370/464 |
| 2006/0041450 | A1 | * | 2/2006 | Dugan ............................. | 705/2 |

FOREIGN PATENT DOCUMENTS

| JP | 10-014890 | 1/1998 |
| JP | 11-299791 | 11/1999 |
| JP | 3072329 U | 7/2000 |

(Continued)

OTHER PUBLICATIONS

Timmons, Deborah et al. "Examinsight for Microsoft MCSE Certifcation Exam 70-210", TotalRecall Publications, Friendwood, TX, USA (Feb. 2003). (ProQuest search NPL).*

(Continued)

*Primary Examiner* — Mark Holcomb
(74) *Attorney, Agent, or Firm* — Holtz, Holtz, Goodman + Chick, PC

(57) ABSTRACT

A technology that prevents leak of patient data, which is personal information, stored in a storage medium without requiring labor is disclosed. According to the technology, when a command for bulk-deleting pieces of data stored in memories 4 to 7 is entered using an operating unit 1 (Step 1), the pieces of data stored in the memories are bulk-deleted (Step S2). When a hospital name, a language to be used, a time zone, preset data, or user-customized data registered in advance is changed, a device is judged to have been resold. The pieces of data stored in the memories are bulk-deleted (Step 2).

1 Claim, 5 Drawing Sheets

(56) References Cited

FOREIGN PATENT DOCUMENTS

| | | | | |
|---|---|---|---|---|
| JP | 2000-254127 | A | 9/2000 | |
| JP | 2000-271120 | A | 10/2000 | |
| JP | 2001-276059 | A | 10/2001 | |
| JP | 2001276059 | A * | 10/2001 | ............... A61B 8/00 |
| JP | 2001-325372 | | 11/2001 | |
| JP | 2003-510145 | A | 3/2003 | |
| JP | 2003-527184 | A | 9/2003 | |
| JP | 2004-128548 | A | 4/2004 | |
| JP | 2004128548 | A * | 4/2004 | ............... H04N 1/00 |

OTHER PUBLICATIONS

International Search Report Dated Jul. 11, 2006.

* cited by examiner

ULTRASONOGRAPHIC DEVICE

TECHNICAL FIELD

The present invention relates to an ultrasonographic device that stores various kinds of patient data, such as an ultrasonic diagnostic image, in a storage medium and uses the stored patient data.

BACKGROUND ART

Large-capacity storage media have become popular in recent years. In ultrasonographic devices, various kinds of patient data, such as an ultrasonic diagnostic image, are stored in storage media provided within the device or externally and the stored patient data are used. FIG. 8 shows an ultrasonographic device described in Patent Document 1 as an example of data to be stored. The device includes a patient report data memory 14, a fetus/normal build data memory 15, a fetus pictogram data memory 16, and a fetus standard deviation pictogram data memory 17. In FIG. 8, reference number 1 indicates an operating unit. Reference number 2 indicates an echo image processing unit. Reference number 3 indicates a central processing unit. Reference number 8 indicates an echo measuring unit. Reference number 9 indicates an image display processing unit. Reference number 11 indicates a display unit.

Patent Document 1: Japanese Patent Application Publication No. Heisei 11-299791 (Abstract)

However, in a conventional ultrasonographic device, when the ultrasonographic device is discarded, resold, or the like, there is risk of patient data, which is personal information, stored in the storage medium being leaked. To delete the patient data stored in the storage medium when the ultrasonographic device is discarded or resold, each piece of data is required to be individually deleted. Alternatively, the storage medium itself is required to be destroyed. Therefore, a large amount of labor is required and complete deletion of the data cannot be conducted. Moreover, the method of destroying the storage medium itself is not applicable when the ultrasonographic device is resold.

DISCLOSURE OF THE INVENTION

The present invention has been achieved in light of the above-described problems of the conventional example. An object of the present invention is to provide an ultrasonographic device that can prevent leak of patient data, which is personal information, stored in a storage medium without requiring labor, thereby enhancing security.

In order to achieve the object, according to the present invention, an ultrasonographic device that stores patient data in a storage medium and uses the stored patient data includes an inputting means and a bulk-deleting means. The inputting means is used to enter a command for bulk-deleting the patient data stored in the storage medium. The bulk-deleting means allows bulk deletion of the patient data stored in the storage medium when the bulk-deletion command is entered via the inputting means.

As a result of the configuration, when a bulk deletion command is entered, the patient data stored in the storage medium can be bulk-deleted. Therefore, leak of patient data, which is personal information, stored in a storage medium can be prevented without requiring labor, thereby enhancing security.

In order to achieve the object, according to the present invention, an ultrasonographic device that stores patient data in a storage medium, uses the stored patient data, and allows a user to register a hospital name includes a bulk-deleting means. The bulk-deleting means allows bulk deletion of the patient data stored in the storage medium when a hospital name that is already registered is changed.

As a result of the configuration, when the hospital name that is already registered is changed, the device is judged to be resold and the patient data stored in the storage medium can be bulk-deleted. Therefore, leak of patient data, which is personal information, stored in the storage medium can be prevented without requiring labor, thereby enhancing security.

In order to achieve the object, according to the present invention, an ultrasonographic device that stores patient data in a storage medium, uses the stored patient data, and allows a user to register a language to be used includes a bulk-deleting means. The bulk-deleting means allows bulk deletion of the patient data stored in the storage medium when a language to be used that is already registered is changed.

As a result of the configuration, when the language to be used that is already registered is changed, the device is judged to be resold and the patient data stored in the storage medium can be bulk-deleted. Therefore, leak of patient data, which is personal information, stored in the storage medium can be prevented without requiring labor, thereby enhancing security.

In order to achieve the object, according to the present invention, an ultrasonographic device that stores patient data in a storage medium, uses the stored patient data, and allows a user to register a time zone includes a bulk-deleting means. The bulk-deleting means allows bulk deletion of the patient data stored in the storage medium when a time zone that is already registered is changed.

As a result of the configuration, when the time zone that is already registered is changed, the device is judged to be resold and the patient data stored in the storage medium can be bulk-deleted. Therefore, leak of patient data, which is personal information, stored in the storage medium can be prevented without requiring labor, thereby enhancing security.

In order to achieve the object, according to the present invention, an ultrasonographic device that stores patient data in a storage medium, uses the stored patient data, and allows a user to set preset data includes a bulk-deleting means. The bulk-deleting means allows bulk deletion of the patient data stored in the storage medium when preset data that is already set is changed.

As a result of the configuration, when the preset data that is already set is changed, the device is judged to be resold and the patient data stored in the storage medium can be bulk-deleted. Therefore, leak of patient data, which is personal information, stored in the storage medium can be prevented without requiring labor, thereby enhancing security.

In order to achieve the object, according to the present invention, an ultrasonographic device that stores patient data in a storage medium, uses the stored patient data, and allows a user to set user-customized data includes a bulk-deleting means. The bulk-deleting means allows bulk deletion of the patient data stored in the storage medium when user-customized data that is already set is changed.

As a result of the configuration, when the user-customized data that is already set is changed, the device is judged to be resold and the patient data stored in the storage medium can be bulk-deleted. Therefore, leak of patient data, which is personal information, stored in the storage medium can be prevented without requiring labor, thereby enhancing security.

In the present invention, the patient data stored in the storage medium can be bulk-deleted. Therefore, leak of patient data, which is personal information, stored in the storage medium can be prevented without requiring labor, thereby enhancing security.

BEST MODE FOR CARRYING OUT THE INVENTION

Hereinafter, an embodiment of the present invention will be described with reference to the drawings.

First Embodiment

Figure 1:
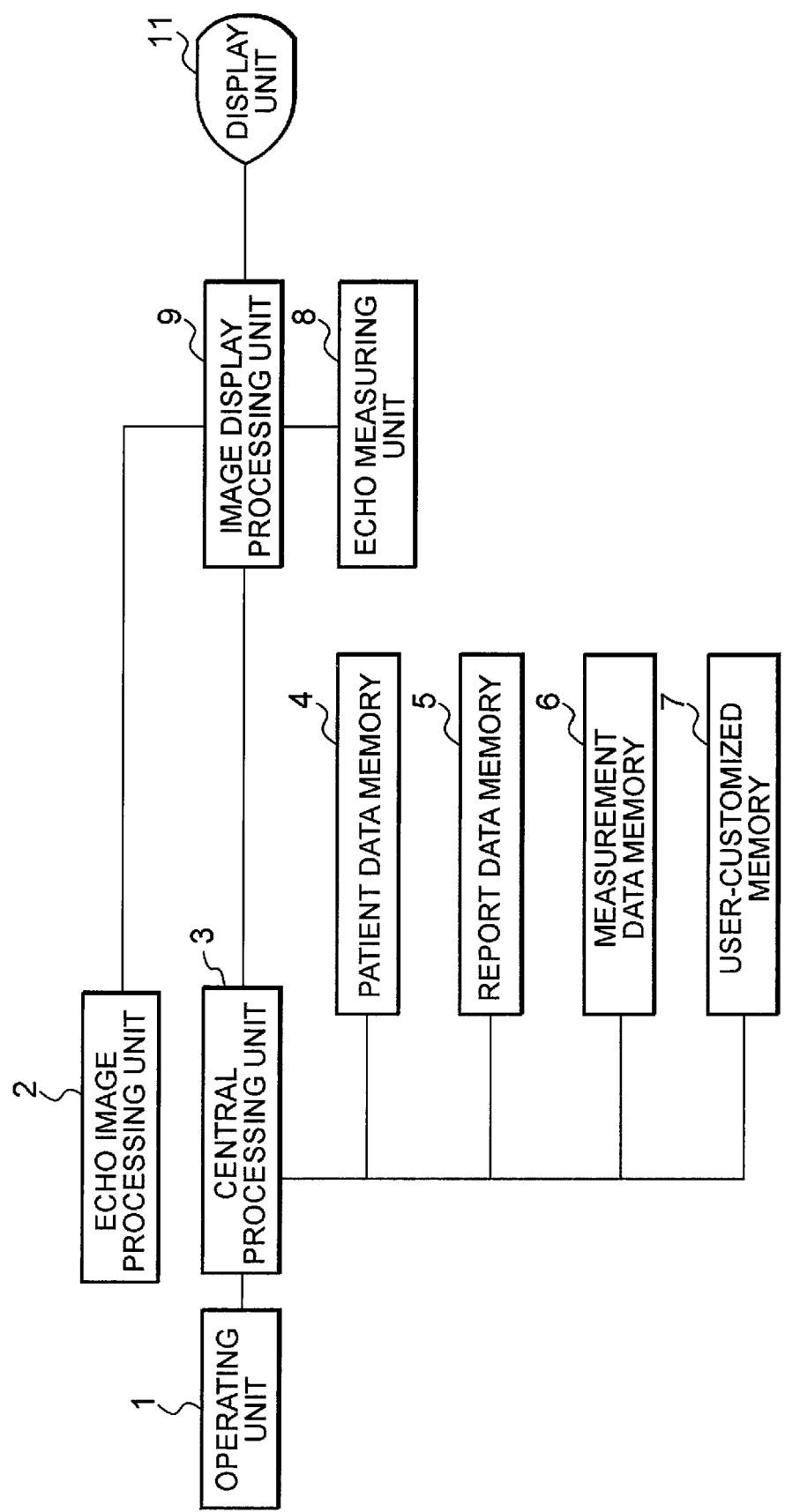
FIG. 1 is a block diagram of an ultrasonographic device according to a first embodiment of the present invention.

FIG. 1 is a block diagram of an ultrasonographic device according to a first embodiment of the present invention.

In FIG. 1, an operating unit 1 includes a keyboard, a trackball, keys, a knob, a liquid crystal display (LCD) displaying unit, and the like. An echo image processing unit 2 generates an echo image by processing echo data loaded via an ultrasonic probe. The echo image processing unit 2 uses a digital scan converter to generate the echo image. A central processing unit 3 controls the operating unit 1, the echo image processing unit 2, and the like. In the example shown in FIG. 1, a patient data memory 4, a report data memory 5, a measurement data memory 6, and a user-customized memory 7 are provided as media storing patient data. An echo measuring unit 8 measures various kinds of data regarding a certain site to be diagnosed within the echo image. An image display processing unit 9 synthesizes the echo image generated by the echo image processing unit 2, the data stored in the memories 4 to 7, and the data measured by the echo measuring unit 8 on a screen to allow the synthesized image to be displayed.

Figure 2:
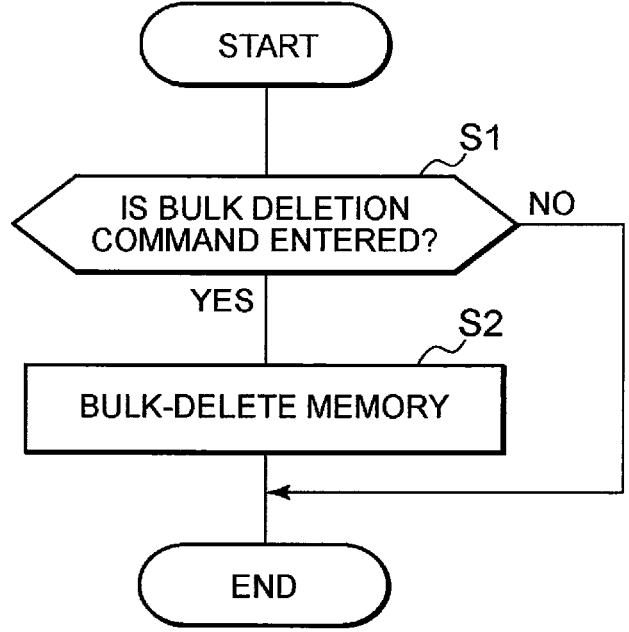
FIG. 2 is a flowchart explaining a process performed by the ultrasonographic device according to the first embodiment.

In the ultrasonographic device configured as described above, as shown in FIG. 2, a function for bulk-deleting pieces of data stored in the memories 4 to 7 is selected. A command corresponding with the bulk deletion is selected and the command is entered using the operating unit 1 (Step S1). The pieces of data stored in the memories 4 to 7 are bulk-deleted (Step S2). Simple operating methods that do not cause erroneous operation are considered as the bulk deletion command entered at Step S1. The operating methods are, for example, a method of displaying a menu screen on the displaying unit 11 and selecting "bulk deletion" from the menu screen, a method of simultaneously pressing a plurality of predetermined keys on the operating unit 1, a method of providing a special key in the operating unit 1, and a method of operating a plurality of predetermined keys in the operating unit 1 in sequence, following a predetermined pattern. When the bulk deletion is performed at Step S2, a deletion confirmation screen can be displayed in advance. Moreover, when a file configuration already includes actual data and index data of the actual data, both of the actual data and the index data are preferably deleted.

As a result of the configuration, the patient data stored in the memories 4 to 7 can be bulk-deleted. Therefore, leak of the patient data, which is personal information, stored in the memories 4 to 7 can be prevented without requiring labor, thereby enhancing security.

Second Embodiment

Figure 3:
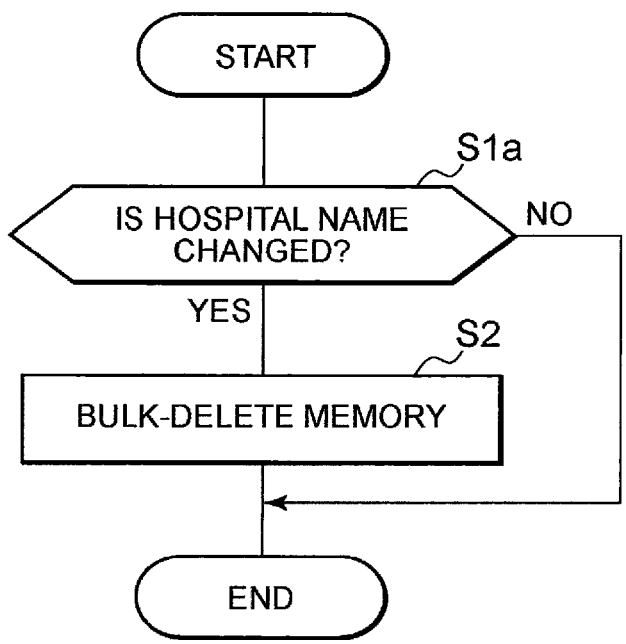
FIG. 3 is a flowchart explaining a process performed by an ultrasonographic device according to a second embodiment.

When the device is reused as a result of being resold, the bulk deletion can be automatically performed. FIG. 3 shows a process according to a second embodiment in which a hospital name can be registered. When a hospital name that is already registered is changed (Step S1a), the device is judged to have been resold. The pieces of data stored in the memories 4 to 7 are bulk-deleted (Step S2).

Third Embodiment

Figure 4:
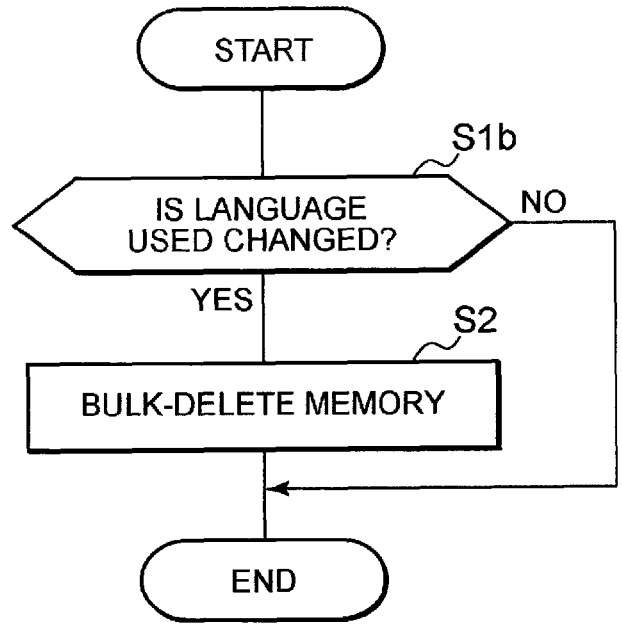
FIG. 4 is a flowchart explaining a process performed by an ultrasonographic device according to a third embodiment.

FIG. 4 shows a process according to a third embodiment in which a language to be used can be registered. When a language to be used that is already registered is changed (Step S1b), the device is judged to have been resold. The pieces of data stored in the memories 4 to 7 are bulk-deleted (Step S2).

Fourth Embodiment

Figure 5:
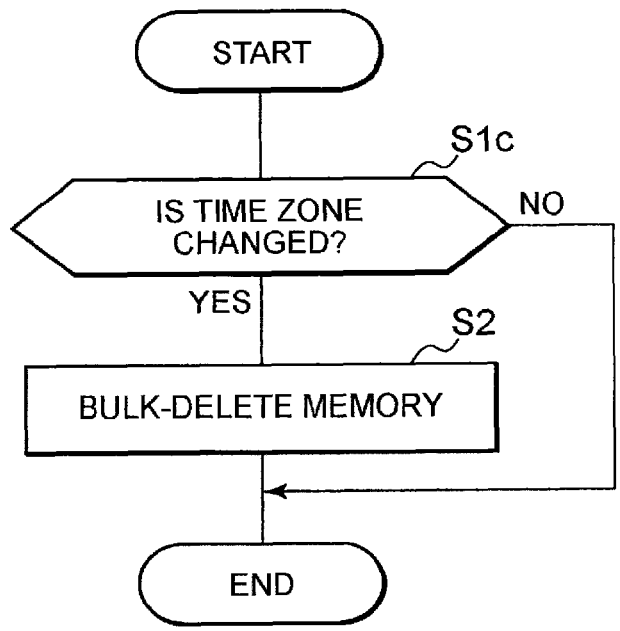
FIG. 5 is a flowchart explaining a process performed by an ultrasonographic device according to a fourth embodiment.

FIG. 5 shows a process according to a fourth embodiment in which a time zone can be registered. When a time zone that is already registered is changed (Step S1c), the device is judged to have been resold. The pieces of data stored in the memories 4 to 7 are bulk-deleted (Step S2).

Fifth Embodiment

Figure 6:
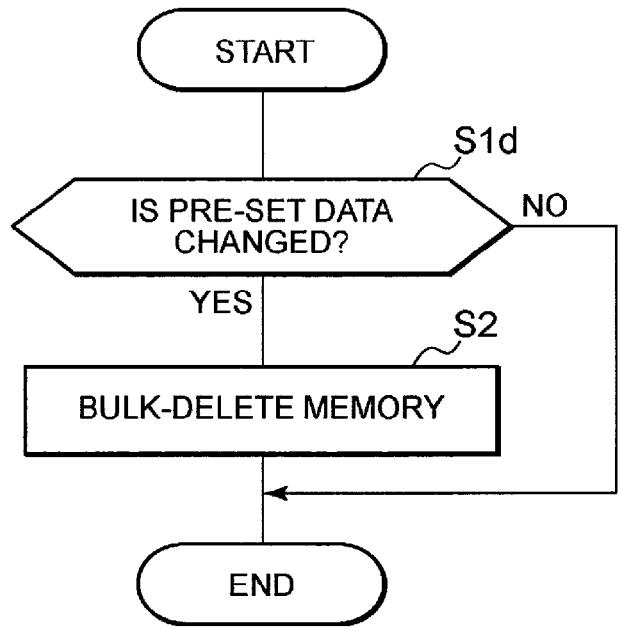
FIG. 6 is a flowchart explaining a process performed by an ultrasonographic device according to a fifth embodiment.

FIG. 6 shows a process according to a fifth embodiment in which various kinds of preset data can be set. When the preset data that is already registered is changed (Step S1d), the device is judged to have been resold. The pieces of data stored in the memories 4 to 7 are bulk-deleted (Step S2).

Figure 7:
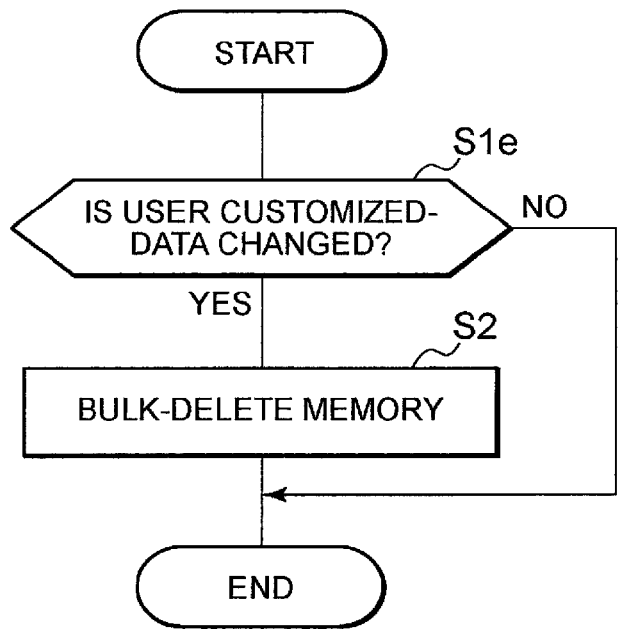
FIG. 7 is a flowchart explaining a process performed by an ultrasonographic device according to a sixth embodiment.
Figure 8:
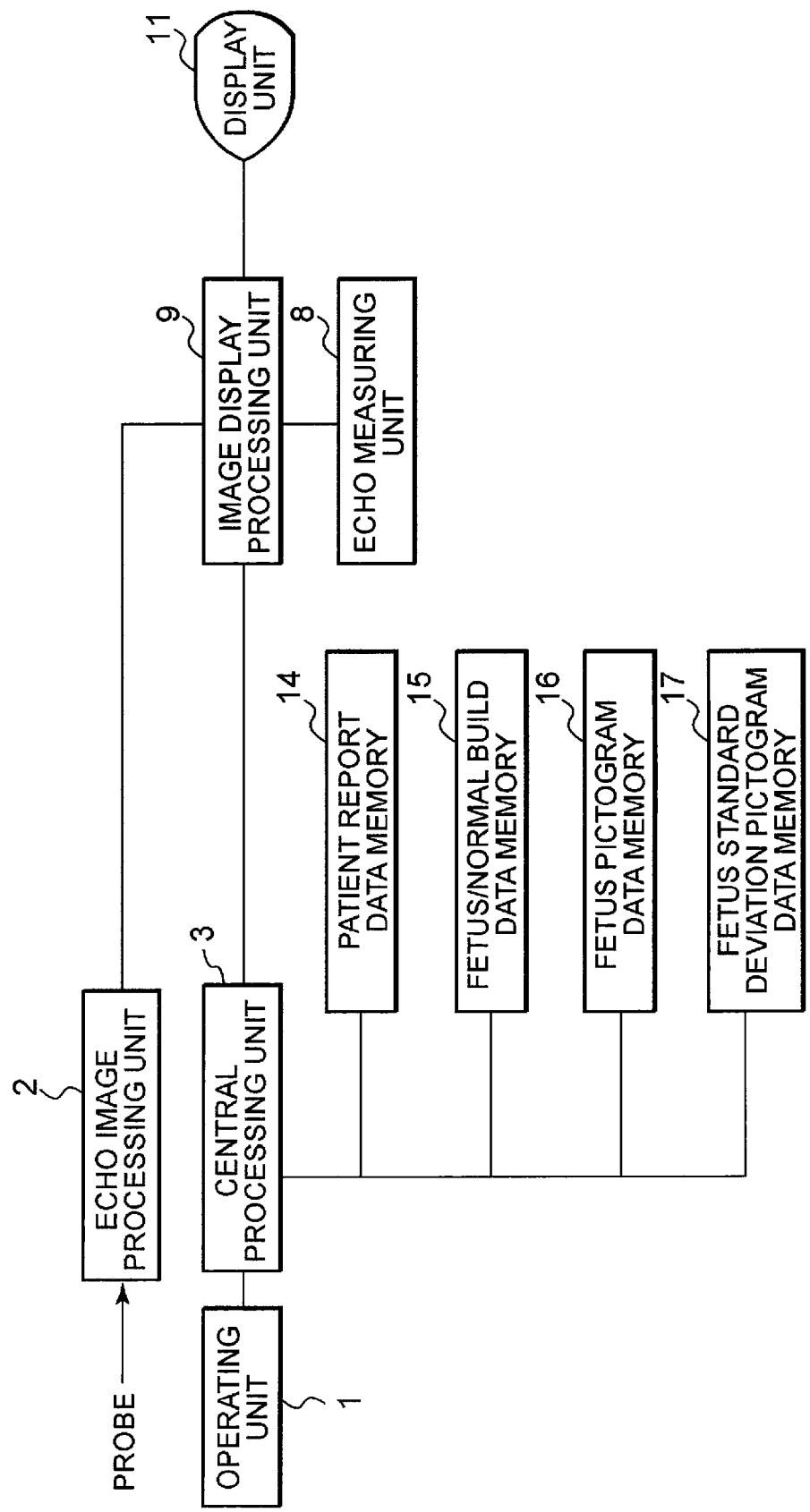
FIG. 8 is a block diagram of a conventional ultrasonographic device.

FIG. 7 shows a process performed by a device in which various kinds of user-customized data can be set. When the user-customized data that is already registered is changed (Step S1e), the device is judged to have been resold. The pieces of data stored in the memories 4 to 7 are bulk-deleted (Step S2).

INDUSTRIAL APPLICABILITY

The present invention bulk-deletes patient data stored in a storage medium. The present invention achieves effects in which leak of patient data, which is personal information, stored in the storage medium can be prevented without requiring labor, thereby enhancing security. Therefore, the present invention can be used in an ultrasonographic device and the like.

The invention claimed is:

1. A method of bulk-deleting patient data stored by an ultrasonographic device, the method comprising:

storing patient data for a plurality of different patients in a storage medium comprising a plurality of individual memory units, said patient data comprising actual data related to the plurality of different patients and index data of the actual data;

using the ultrasonographic device, receiving a user-specified setting that comprises a registered time zone of the ultrasonic device by a first entity;

wherein the ultrasonographic device is configured to:
  (i) initiate bulk deletion of the patient data in response to receiving a manually-entered command expressly instructing the processing unit to bulk delete the patient data, and
  (ii) initiate bulk deletion of the patient data for each of the plurality of patients stored in the storage medium in response to receiving an instruction to change the user-specified setting that comprises a registered time zone of the ultrasonic device entered through manual manipulation of at least one of a keyed data-entry device and a computer pointing device, indicating a change of the ownership of the ultrasonographic device to a second entity that is different than the first entity, further wherein said bulk deletion of the patient data comprises deletion of both the actual data relating to the plurality of different patients and the index data of the actual data.

* * * * *